United States Patent [19]
Butler et al.

[11] Patent Number: 6,096,937
[45] Date of Patent: Aug. 1, 2000

[54] PROCESS FOR DEHYDROGENATION OF ETHYLBENZENE TO STYRENE

[75] Inventors: James R. Butler, Houston; Joseph David Korchnak, Sugar Land, both of Tex.

[73] Assignee: Fina Technology, Inc., Dallas, Tex.

[21] Appl. No.: 09/195,179

[22] Filed: Feb. 8, 1999

Related U.S. Application Data

[63] Continuation of application No. 08/745,356, Nov. 8, 1996, abandoned.

[51] Int. Cl.⁷ .......................... C07C 5/327; C07C 5/333
[52] U.S. Cl. ...................... 585/440; 585/441; 585/444; 585/911
[58] Field of Search .................... 585/440, 441, 585/444, 911

[56] References Cited

U.S. PATENT DOCUMENTS

| | | | |
|---|---|---|---|
| 3,288,871 | 11/1966 | Soderquist et al. | 585/444 |
| 3,326,996 | 6/1967 | Henry et al. | 585/441 |
| 3,330,878 | 7/1967 | Huckins, Jr. et al. | 585/441 |
| 3,417,156 | 12/1968 | Berger | 585/911 |
| 3,755,482 | 8/1973 | Nunnally et al. | 585/441 |
| 3,855,330 | 12/1974 | Mendelsohn et al. | 585/441 |
| 3,868,428 | 2/1975 | Cox | 585/441 |
| 4,287,375 | 9/1981 | Moller et al. | 585/440 |
| 4,549,032 | 10/1985 | Moeller et al. | 585/445 |
| 5,242,574 | 9/1993 | Broutin et al. | 208/48 R |

*Primary Examiner*—Walter D. Griffin
*Attorney, Agent, or Firm*—Michael J. Caddell; M. Norwood Cheairs

[57] ABSTRACT

The present invention discloses a method and apparatus for dehydrogenating ethylbenzene into styrene which method and apparatus eliminate the need for multiple reactors and preheaters by providing a single compact reactor which utilizes the principle of ascending-heat thermal reactor by having an internal heat source such as gas heaters or electric elements.

6 Claims, 1 Drawing Sheet

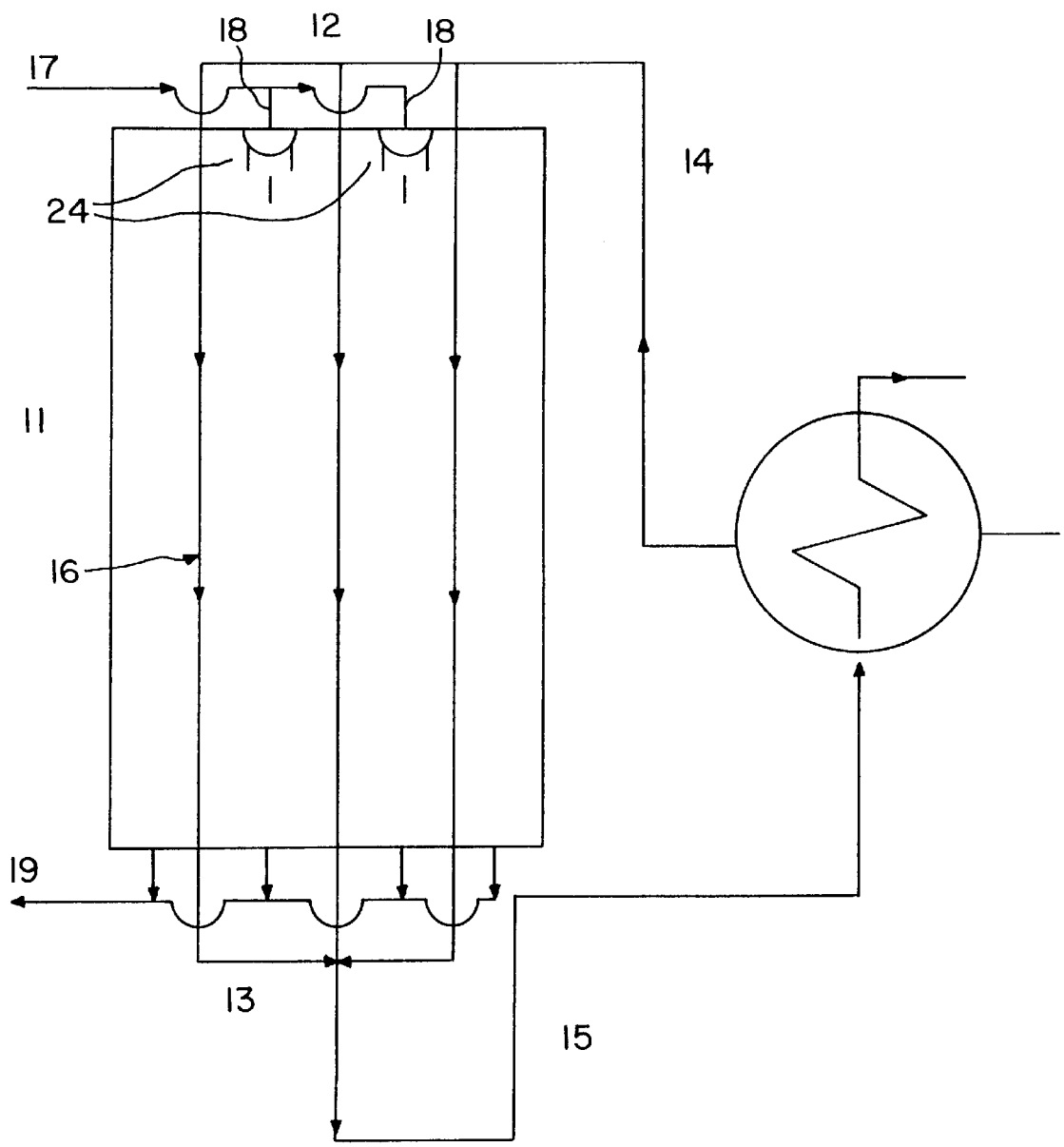

PROCESS FOR DEHYDROGENATION OF ETHYLBENZENE TO STYRENE

CROSS REFERENCE TO RELATED APPLICATION

This application is a continuation of a prior-filed application of the same title, Ser. No. 08/745,356, filed Nov. 8, 1996, in the name of Butler, et al., now abandoned.

BACKGROUND OF THE INVENTION

This invention relates to the field of styrene manufacture and more particularly discloses methods and apparatus, including reactor vessels, for the dehydrogenation of ethylbenzene into styrene monomer.

It is well known in the art of styrene manufacture to react ethylbenzene ("EB") over a dehydrogenation catalyst such as iron oxide under elevated temperatures in the range of 1000–1230° F. and at a pressure of about 4 to 20 PSIA in order to strip hydrogen from the ethyl-radical on the benzene ring to form the styrene molecule. This might normally be done in a series of radial adiabatic styrene reactors which are commonly termed EB dehydro reactors. The dehydro reactors generally are elongated, cylindrical, vertical structures of a very large size, ranging in diameter from about five to about thirty feet or more, and in length from about ten feet to about one hundred feet or more. The normal construction for such a reactor allows for input of the ethylbenzene gas at an inlet located in the center of the vertical reactor, whereupon the gas is flowed radially outward through an annular area, passing through an annular porous catalyst bed of iron oxide or other suitable dehydro catalyst, and then passing through an outer annular area to exit the reactor shell. Since the flow of ethylbenzene across the catalyst bed is in a radial direction, these reactors are sometimes identified as "radial" reactors.

It is currently believed by those skilled in the art of styrene manufacture that the optimum arrangement of multiple, radial bed, EB reactors with typical dehydro catalyst beds is to utilize three or more radial adiabatic reactors arranged in serial-flow orientation, with reheat means between the reactors to add heat to the endothermic reaction. Each reactor may have a different selectivity catalyst from the catalyst of the other reactors. "Selectivity" in this instance is considered by one skilled in the art to mean the ability of the catalyst to selectively produce higher levels of the desirable styrene and lower levels of the undesirable toluene and benzene. "Activity" is considered to be the ability of the catalyst to convert a certain percentage of ethylbenzene to aromatics for each pass of feedstock over the catalyst. An example of the conventional radial reactor referred to above is that found in U.S. Pat. No. 5,358,698 to Butler, et al.

Because of the adiabatic design of conventional EB reactors and the endothermic nature of the dehydrogenation reaction, conventional EB processes require the addition of heat to the process to maintain the dehydrogenation reaction. This, in turn, necessitates the use of multiple reactors in order to provide opportunity to add heat during the process, which is accomplished by utilizing heaters or "superheaters" located between each of the serial reactors. This is also one reason that different catalysts are used in each of the serial reactors, with catalyst selectivity varying between the several reactors. Due to the endothermic nature of the EB reaction in the radial reactors, the liquid hourly space velocity (LHSV) through the system is severely limited. The EB feed must be flowed through the reactors slowly enough to allow dehydrogenation to be substantially completed, which is slowed by the absorption of heat in the reaction.

Therefore, a need has been felt for a process of dehydrogenating ethylbenzene which does not require large multiple reactors, heaters, heat exchangers, or multiple catalysts, and which is not limited by low LHSVs.

SUMMARY OF THE INVENTION

The present invention discloses a process and apparatus for dehydrogenation of ethylbenzene using a single, small catalytic reactor which is neither adiabatic nor isothermal, but in fact, is an ascending-heat reactor.

BRIEF DESCRIPTION OF THE DRAWING

The figure is a cross sectional view of the reactor and process flow diagram for practicing the present invention.

DESCRIPTION OF THE PREFERRED EMBODIMENTS

Referring to the drawing which is a cross-sectional schematic diagram showing the concept of the present invention, an ascending-heat EB reactor is disclosed having a reaction chamber defined by an external shell 11, with an inlet header 12 and an exit header 13. A supply line 14 communicates with inlet header 12 and a product flow line 15 exits outlet header 13.

The central section of EB reactor consists of a furnace 11 inside which is located a series of product flow tubes 16 which are connected to the inlet header 12. The open bore of tube 16 is exposed to the inlet header 12 allow EB feed to enter through line 14 into inlet header 12 and to traverse tubes 16 into outlet header 13. Although, only three of such tubes are disclosed in this schematic drawing, in actual practice a large multitude of such tubes would be provided in the reactor. Above tubes 16 are a plurality of heaters 18 at the top of the furnace box. Heater tubes 18 have a source of fuel such a natural gas, hydrogen, or other combustible gas which is provided by means of fuel inlet line 17 communicating with heater elements 18. A combustion products exhaust line 19 communicates through the wall of chamber 11 to carry the products of combustion from the flames of nozzles 24. A source of oxygen may also be provided by means of a separate oxygen supply line or air supply line which may be connected to burner tubes 18 separately or may be passed through a mixer box prior to entering line 17 where air or oxygen can be mixed with the gaseous fuel.

In typical operation, ethylbenzene feed material is provided through inlet line 14 and passes reactor tubes 16. The interior of reactor tubes 16 may be completely or partially filled with the desirable EB dehydro catalyst that the operator wishes to utilize in the process. Those skilled in the art are aware of suitable dehydro catalysts which can be advantageously utilized in the present invention.

As previously mentioned, reactor tube 16 may be completely or partially filled with the desirable EB dehydro catalyst so that EB feed from inlet header 12 flows through tube 16 across the chosen catalyst and is collected in outlet header 13.

While EB flows through reactor tube 16, the gaseous mixture of fuel and oxygen source entering line 17 moves into heater nozzles 24 and exits. An ignition source is provided upon startup of the reactor and the gas is continuously passed through nozzles 24 and burns as it exits the nozzles. A minor amount of experimentation can determine the particular nozzle sizes to use for obtaining an ascending-heat thermal reactor. Thus, as ethylbenzene enters line 14 and passes through chamber inlet header 12 into reactor tube 16, it is passed across the EB dehydro catalyst contained in the reactor tube 16 and subjected to an increasing level of heat input due to the gaseous fuel being consumed. Although gaseous fuel is desirable, it is of course possible to use a liquid fuel, which can be atomized by the oxygen source gas at a point prior to entering line 17. Other conventional nozzle-heater arrangements can be used to consume different fuel sources. In addition, it is possible that, rather than a chemically-driven heat supply, one could substitute electrical heating elements which vary in heat generation from the input end of the reactor to the output end of the reactor, to obtain the increasing heat supply for the reactor. Thus, one skilled in the art could substitute electrical heating elements for heating tubes 18 with increasing heat output towards the end of the heating elements associated with the output end of the reactor tube 16.

In the present invention, however, it is desirable to use a heat source that is compatible with the refining operations around the EB dehydro system where the most available fuel is usually hydrogen or a compressed natural gas and therefore the description is defined in terms of a gas-fired heating system. Upon traversing the length of reactor tube 16 across the catalyst contained therein, a substantial dehydrogenation of the ethylbenzene feed is accomplished and the product exiting into outlet header contains substantial styrene, which is then passed through product flow line 15 for further purification and removal of non-styrene products such as ethylbenzene, benzene, toluene and hydrogen. As previously mentioned, the combustion gases exiting nozzle 24 flow out through gas exhaust conduit 19 in the bottom of the heater box. Thus is described a reactor for dehydrogenating ethylbenzene into styrene which is defined as an ascending-heat reactor to provide heat input for the endothermic ethylbenzene dehydrogenation reaction and furthermore, to provide increasing amounts of heat towards the end of the EB dehydro reaction as the components being reacted are being used up and the reaction becomes harder to drive.

Although certain preferred embodiments of the present invention have been herein described in order to provide an understanding of the general principals of the invention, it will be appreciated that various changes and innovations can be affected in the described dehydrogenation reactor system without departing from these principals. It is also possible to vary the flow rate through the tubes (LHSV) by varying the diameter of the reactor tubes along their length. For example, the reactor tubes could be smaller at the inlet end and larger at the outlet end to provide a decreasing LHSV down the length of each reactor tube. This would allow the ethylbenzene reaction to have a longer residence time at the higher temperatures in the tubes. Alternatively, it would be possible to vary the tubes diameter in the opposite direction by having the tubes larger at the beginning and smaller at the end to increase the LHSV down the length of the tube. Other changes would be apparent to one skilled in the art and therefore the invention is declared to cover all changes and modifications of the specific examples of the invention herein disclosed for purposes of illustration, which do not constitute departure from the spirit and scope of the invention.

The embodiments of the present invention in which an exclusive property or privilege is claimed are defined as follows:

What is claimed is:

1. A process for the dehydrogenation of ethylbenzene to styrene, said process comprising:
    passing ethylbenzene feedstock through at least one dehydrogenation reactor tube containing a dehydrogenation catalyst, said at least one tube being located inside and spaced apart from the interior wall of a reactor vessel;
    applying a varying amount of heat along the length of said tube by heating sources located between said tube and said reactor vessel; and
    recovering styrene product at the end of said tube;
    wherein said varying amount of heat varies along the length of said tube in increasing increments along the length thereof in the direction of flow of said feedstock through said tube; and,
    wherein said heat is sufficient to convert said ethylbenzene to styrene.

2. The process of claim 1 wherein said tube is of a substantially constant cross-sectional area along its length and the heat applying step is achieved by the burning of a fluidic fuel in a variable burner communicating with the area between said tube and said reactor vessel.

3. The process of claim 1 wherein said tube is of a substantially constant cross-sectional area along its length and the heat applying step is achieved by energizing at least two discrete electrical heating elements located along the length of said tube, in the space between said tube and said reactor vessel.

4. The process of claim 1 wherein said varying step comprises varying the LHSV of the ethylbenzene feedstock through the tube by using a tube having varying cross-sectional area along at least a portion of its length.

5. The process of claim 2 wherein said burning of fluidic fuel is achieved by spraying said fuel alongside said tube in the direction of flow of feedstock in said tube.

6. The process of claim 5 wherein said fluidic fuel is a fuel gas.

* * * * *